(12) United States Patent
Gerberding

(10) Patent No.: US 6,475,187 B1
(45) Date of Patent: Nov. 5, 2002

(54) CONVERTIBLE CATHETER INCORPORATING DISTAL FORCE TRANSFER MECHANISM

(75) Inventor: Brent C. Gerberding, Minneapolis, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/034,419

(22) Filed: Mar. 4, 1998

(51) Int. Cl.[7] .................. A61M 29/00; A61M 25/00; A61B 6/00
(52) U.S. Cl. .................. 604/102.02; 604/103.09; 604/524; 604/264; 606/194; 600/435
(58) Field of Search .................. 604/264, 102, 604/103, 523, 524, 280, 96, 525, 528; 606/191, 192, 193, 194, 195, 196, 197, 198; 600/433, 434, 435, 585

(56) References Cited

U.S. PATENT DOCUMENTS

| | | | |
|---|---|---|---|
| 4,582,181 A | 4/1986 | Samson | 128/348.1 |
| 4,748,982 A | 6/1988 | Horzewski et al. | 128/344 |
| 4,762,129 A | 8/1988 | Bonzel | 128/344 |
| 4,819,751 A | 4/1989 | Shimada et al. | 128/344 |
| 4,906,241 A | 3/1990 | Noddin et al. | 606/194 |
| 4,917,088 A | 4/1990 | Crittenden | 606/194 |
| 4,917,666 A | 4/1990 | Solar et al. | 604/95 |
| 4,955,895 A | 9/1990 | Sugiyama et al. | 606/194 |
| 4,964,409 A | 10/1990 | Tremulis | 128/657 |
| 4,998,917 A | 3/1991 | Gaiser et al. | 604/96 |
| 4,998,923 A | 3/1991 | Samson et al. | 606/194 |
| 5,002,532 A | 3/1991 | Gaiser et al. | 604/101 |
| 5,019,042 A * | 5/1991 | Sahota | 604/101 |
| 4,762,129 A | 7/1991 | Bonzel | 206/194 |
| 5,040,548 A | 8/1991 | Yock | 128/898 |
| 5,042,985 A | 8/1991 | Elliott et al. | 606/192 |
| 5,135,535 A | 8/1992 | Kramer | 606/194 |
| 5,176,637 A | 1/1993 | Sagae | 604/96 |

(List continued on next page.)

FOREIGN PATENT DOCUMENTS

| | | |
|---|---|---|
| EP | 0 405 831 B1 | 6/1995 |
| WO | WO 92/17236 | 10/1992 |
| WO | WO 92/22345 | 12/1992 |
| WO | WO 93/20882 | 10/1993 |
| WO | WO 94/03213 | 2/1994 |
| WO | WO 94/04216 | 3/1994 |

*Primary Examiner*—Angela D. Sykes
*Assistant Examiner*—Patricia Bianco
(74) *Attorney, Agent, or Firm*—Crompton, Seager & Tufte, LLC

(57) ABSTRACT

A method and apparatus for increasing the force transmission from a core wire to a more proximal portion of the catheter, and for directly providing column support at or near the side port of a convertible or rapid-exchange type of catheter. A core wire is typically attached to a proximal portion of a catheter, and extends distally therefrom through a lumen in the catheter. In accordance with the present invention, the core wire has a size and shape relative the lumen of the catheter such that the lateral movement of the core wire is restricted in a restriction region. By restricting the core wire at a distal location relative to the proximal catheter portion, the force transmission from the core wire to the proximal catheter portion can be increased. Further, in a rapid exchange or convertible type configuration, the restriction region may be placed proximate the side hole. By restricting the movement of the core wire adjacent to the side hole, the core wire can provide direct column support thereto reducing the likelihood of kinking or the like at that location.

32 Claims, 5 Drawing Sheets

U.S. PATENT DOCUMENTS

| | | | |
|---|---|---|---|
| 5,209,728 A | | 5/1993 | Kraus et al. .................. 604/96 |
| 5,217,482 A | * | 6/1993 | Keith ........................ 606/194 |
| 5,242,396 A | | 9/1993 | Evard ........................ 604/96 |
| 5,277,199 A | * | 1/1994 | DuBois et al. .............. 128/772 |
| 5,328,468 A | | 7/1994 | Kaneko et al. .............. 604/96 |
| 5,328,472 A | * | 7/1994 | Steinke et al. ............. 604/102 |
| 5,364,376 A | | 11/1994 | Horzewski et al. ......... 604/280 |
| 5,382,234 A | | 1/1995 | Cornelius et al. ............ 604/96 |
| 5,389,087 A | | 2/1995 | Miraki ...................... 604/247 |
| 5,395,335 A | | 3/1995 | Jang .......................... 604/102 |
| 5,423,754 A | * | 6/1995 | Cornelius et al. ........... 604/103 |
| 5,425,711 A | | 6/1995 | Ressemann et al. ......... 604/96 |
| 5,456,680 A | | 10/1995 | Taylor et al. ................. 606/2 |
| 5,458,613 A | | 10/1995 | Gharibadeh et al. ........ 606/194 |
| 5,458,639 A | * | 10/1995 | Tsukashima et al. ......... 604/97 |
| 5,470,315 A | | 11/1995 | Adams ....................... 604/96 |
| 5,489,271 A | | 2/1996 | Andersen .................... 604/102 |
| 5,496,275 A | | 3/1996 | Sirhan et al. ................. 604/96 |
| 5,507,301 A | * | 4/1996 | Wasicek et al. ............. 128/772 |
| 5,545,134 A | | 8/1996 | Hilaire et al. ................ 604/96 |
| 5,545,138 A | | 8/1996 | Fugoso et al. .............. 604/102 |
| 5,549,552 A | | 8/1996 | Peters et al. ................. 604/96 |
| 5,569,201 A | | 10/1996 | Burns ......................... 604/96 |
| 5,667,493 A | * | 9/1997 | Janacek ...................... 604/96 |
| RE35,648 E | * | 11/1997 | Tenerz et al. ............... 128/673 |
| 5,776,100 A | * | 7/1998 | Forman ...................... 604/102 |
| 5,931,812 A | * | 8/1999 | Andersen et al. ........... 604/102 |
| 5,931,892 A | * | 8/1999 | Andersen et al. |
| 5,980,484 A | * | 11/1999 | Reesemann et al. ......... 604/96 |
| 6,066,114 A | * | 5/2000 | Goodin et al. .............. 604/102 |
| 6,171,279 B1 | * | 1/2001 | Hilaire et al. |
| 6,190,358 B1 | * | 2/2001 | Fitzmaurice et al. |

\* cited by examiner

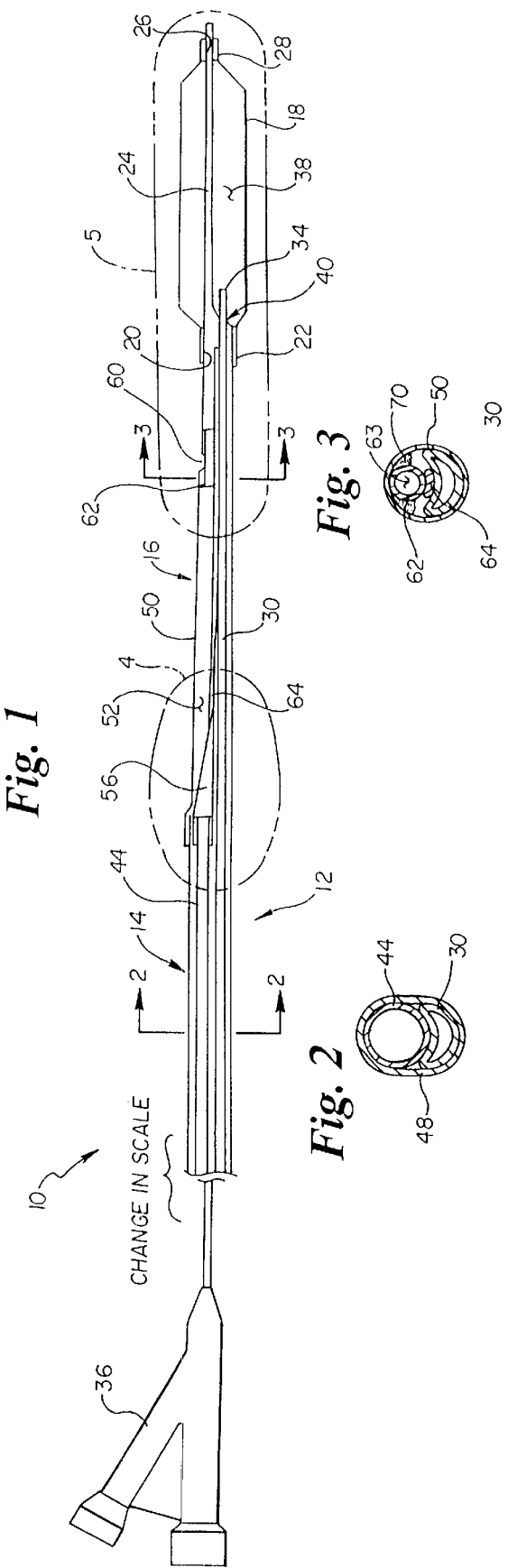

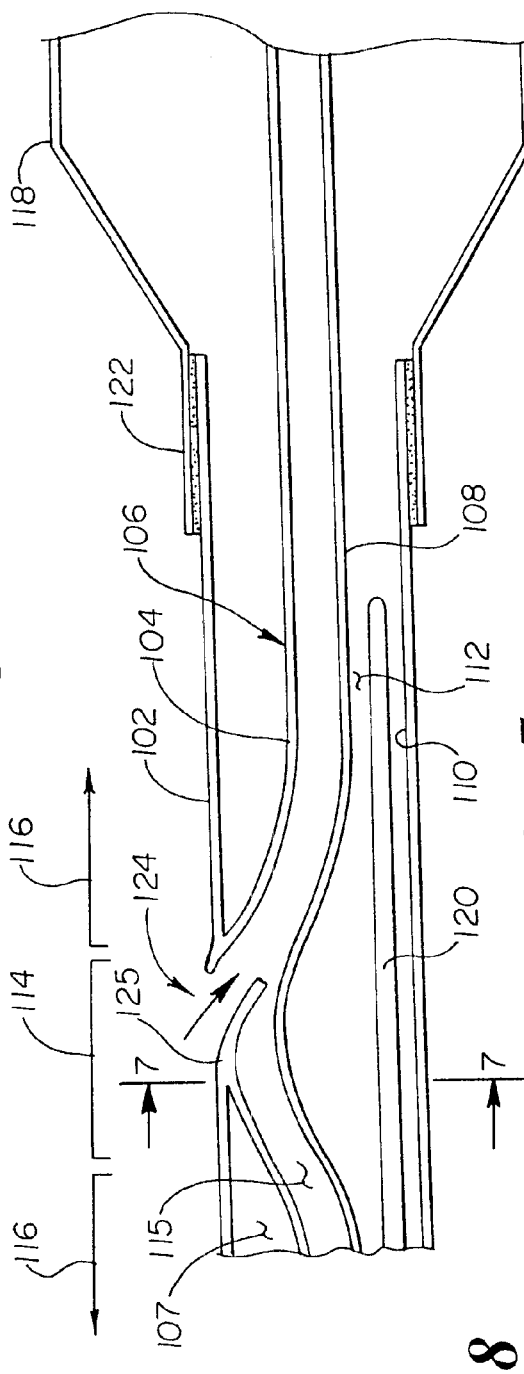
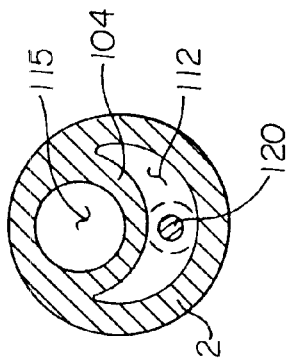
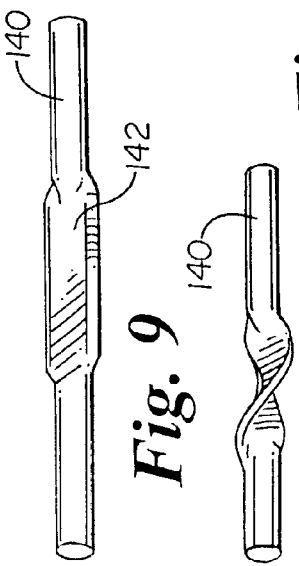
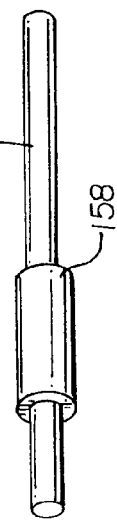

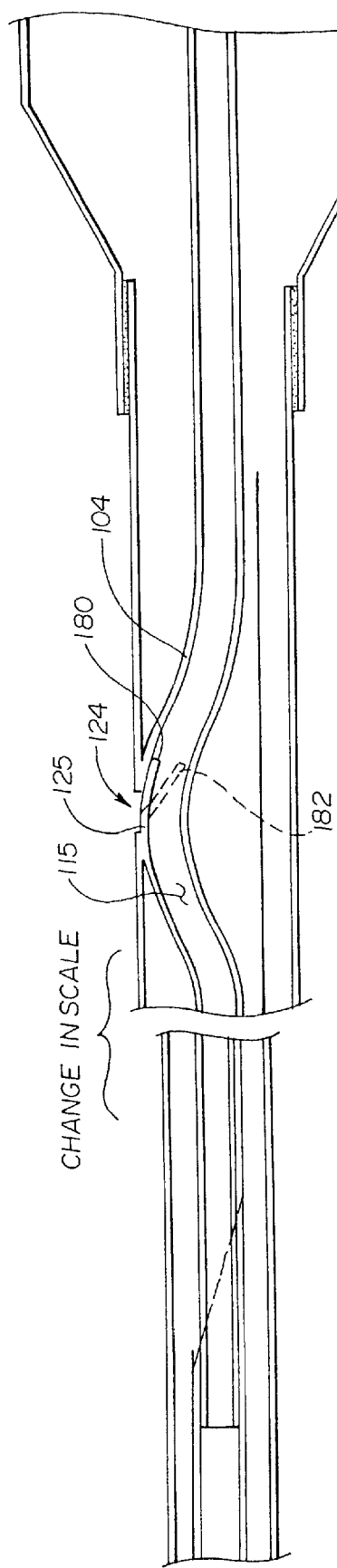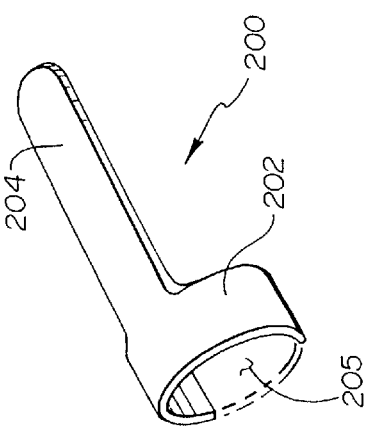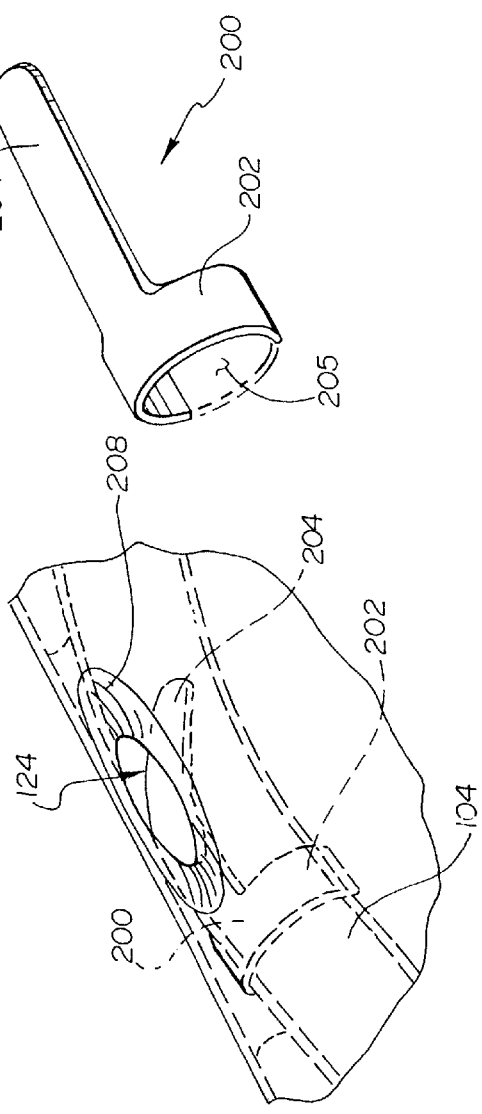

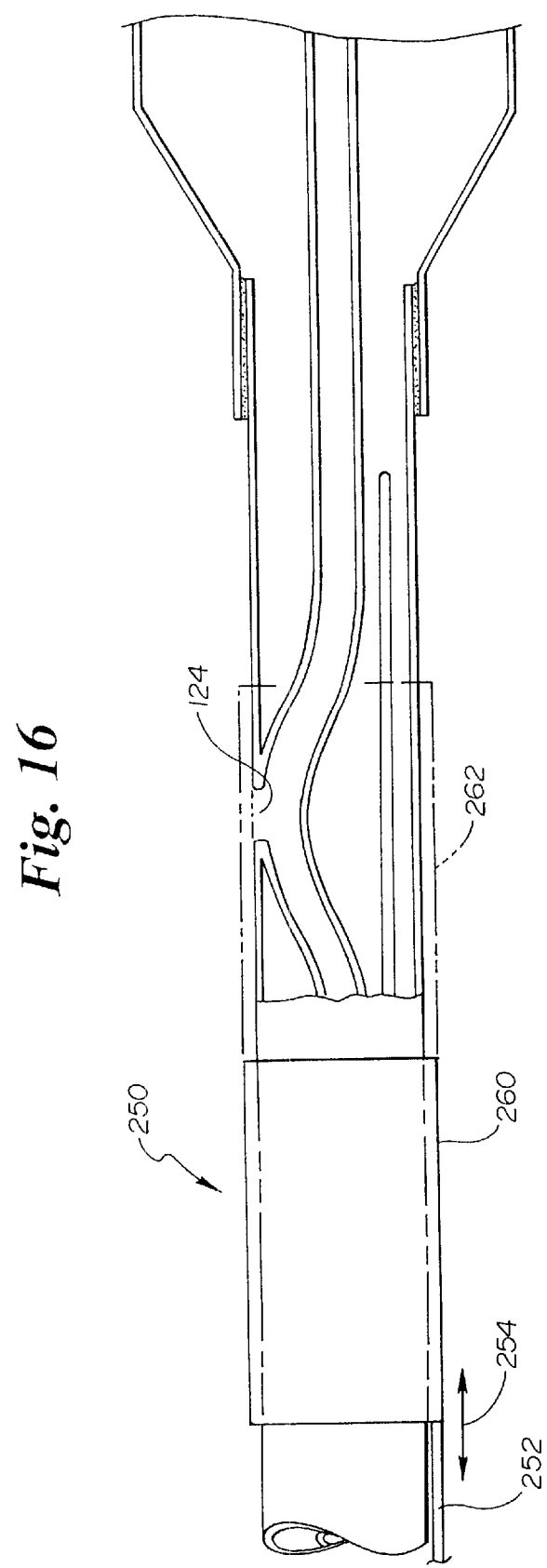

CONVERTIBLE CATHETER INCORPORATING DISTAL FORCE TRANSFER MECHANISM

TECHNICAL FIELD

This invention relates to the field of intravascular medical devices. More specifically, the present invention relates to a convertible catheter incorporating a force transfer mechanism for increasing the force transfer from a distally extending core wire to a proximal portion of the catheter.

BACKGROUND OF THE INVENTION

Intravascular catheterization devices have proven to be useful and efficient for both therapeutic and diagnostic purposes. Intravascular therapeutic techniques, such as angioplasty, atherectomy, and laser irradiation, have been developed as alternatives to bypass surgery for treating vascular diseases or other conditions that occlude or reduce the lumen size of portions of a patient's vascular system. In particular, balloon angioplasty has proven to be a useful and in many circumstances a preferred treatment for obstructive coronary diseases. Also, intravascular diagnostic techniques, such as ultrasonic imaging and Doppler blood flow measurements, have been developed to measure or image the extent of an occlusion of a vessel (e.g., stenosis). The devices used to perform the aforementioned intravascular therapeutic and diagnostic techniques may be used together or in conjunction with more invasive techniques such as coronary surgery.

These intravascular therapeutic and diagnostic devices have achieved acceptance because of their effectiveness as well as the fact that they can be used in a minor surgical procedure that is relatively nondisruptive to the patient compared to coronary surgery. These devices rely on the positioning of a catheter into the vascular system of a patient via an incision at an accessible location which may be remote from the site of the occlusion or stenosis. For example, the accessible location may be the femoral artery at the groin. The intravascular device is then advanced through the incision via the femoral artery to a desired coronary distal site. The distal sites into which the device may be advanced include the coronary arteries, branch vessels stemming from the external carotid artery such as the occipital and the arteries leading to the vessels of the head and brain, splenic, and the inferior mesenteric and renal arteries leading to the organs of the thorax as well as other vessels.

Because of the small size of some of these vessels and the tortuous passages through the vessels, positioning of a catheter device through a patient's vasculature can be a difficult and time consuming task requiring considerable skill on the part of the physician. For example, in order to perform an angioplasty dilation, the angioplasty balloon catheter must be positioned across the stenosis in the arterial site. The stenosis may be located in a tortuous portion of the coronary vasculature and, furthermore, the obstructive arterial disease may impede crossing the stenosis with the balloon portion of the angioplasty catheter. Thus, not all arterial obstructions can be successfully treated by present intravascular balloon catheter procedures because some arterial obstructions are not readily accessible to a balloon dilation catheter. Accordingly, there is often a need for intravascular catheters of very low profile that can be positioned in narrow, tortuous regions of a person's vasculature.

Another important consideration relating to intravascular procedures, such as angioplasty, relates to the exchange of various devices used to perform the procedures. Intravascular therapeutic and diagnostic devices come in various types and sizes suitable for the vessel size and location in which the treatment is to be performed. Sometimes, it becomes necessary to exchange a first therapeutic device for one of a different size after an unsuccessful attempt has been made to position the first device in the appropriate location. It may also become necessary to exchange therapeutic devices after the first device is successfully positioned in the desired location. This may be necessitated because it becomes apparent that the first device is the wrong size or configuration, or because it is determined that additional therapeutic or diagnostic procedures with a different size or type of device is required.

Several different types of catheter constructions have been developed for positioning intravascular therapeutic or diagnostic catheters through a patient's vasculature. Two primary types of catheter constructions are the over-the-wire (OTW) type catheters and the single operator exchange (SOE) type catheters.

An over-the-wire type catheter includes a central lumen through the entire length of the intravascular device that can accommodate a separate guide wire that is movable, and removable, in relation to the catheter to facilitate positioning of the catheter in a remote vessel location over the guide wire. In the over-the-wire construction, the catheter typically includes a lumen adapted to receive the guide wire from a proximal end to the distal end of the device. The guide wire is initially loaded through the lumen of the over-the-wire catheter and extends out from the distal end thereof. Then, the guide wire and the intravascular catheter are advanced together and positioned in the vessel at the desired site. The guide wire may be advanced distally of the distal end of the catheter and steered, as necessary, to traverse tortuous passages of the vessel with the catheter subsequently advanced distally over the wire tracking the wires path. With the guide wire extending through the full length lumen, the guide wire provides some column support to the catheter shaft especially in the distal portion thereof. This improves the pushability of the catheter. The guide wire may then be withdrawn proximally through the lumen of the catheter or may be left in place extending from the distal end of the catheter during the procedure.

The over-the-wire type intravascular catheter facilitates exchanges because a first catheter can be exchanged with a second catheter without removing the guide wire. This allows an exchange of catheters without having to repeat the difficult and time consuming task of positioning the guide wire. In order to leave the distal end of the guide wire in place, it is preferred to maintain a hold on a proximal end portion of the guide wire during the exchange operation. One way to maintain such a hold is to use a guide wire having a sufficiently long length (e.g., 300 cm) so that the entire catheter can be completely withdrawn over the guide wire while maintaining a hold on a portion of the wire. A disadvantage of this method is that the long proximally extending portion of the guide wire may be in the way during the procedure. Another way to maintain a hold on a portion of the guide wire during an exchange operation is to use a guide wire extension. A disadvantage of this method is that not all guide wires are adapted to connect to an extension wire, and moreover, the step of connecting the guide wire to the extension wire can sometimes be tedious and difficult to perform.

A second type of catheter which facilitates the exchange of a first catheter with a second catheter is the single-operator exchange type construction. With the single-operator exchange type construction, a guide wire occupies a position adjacent and exterior to the intravascular catheter along proximal and intermediate portions of the catheter and enters into a short guide wire lumen of the catheter via an opening at a location close to a distal portion of the catheter. With this type of construction, the catheter can be positioned in the patient's vessel by positioning a guide wire in the desired location and advancing the catheter device over the wire. An advantage of the short guide wire lumen is that in the event it becomes necessary to exchange the catheter, the position of the guide wire can be maintained during withdrawal of the catheter without the use of a long guide wire (e.g., 300 cm) or an extension wire. Because the proximal end of the guide wire is exterior to the proximal end of the catheter, the proximal end of the guide wire can be held during withdrawal of the catheter so that the position of the distal end of the guide wire in the patient's vessel can be maintained. With this type of catheter, it is necessary that the distance from the distal end of the catheter to the proximal guide wire lumen entrance be less than the length of the guide wire that extends proximally out of the patient.

Although single operator exchange catheters make it easier to exchange catheters, the construction has two disadvantages. First, the guide wire running external to the catheter shaft does not provide any column support for the shaft nor does the shaft provide support for the wire if the wire is pushed distally to cross a lesion. Second, with the single operator exchange design, the guide wire can not be replaced while the catheter remains in the body.

Just as it is sometimes necessary to exchange an intravascular catheter, it may also become necessary to exchange the guide wire or otherwise assist in advancing the guide wire to the desired location in the vessel. After the guide wire and catheter are in the vessel, it may be determined that the size or shape of the guide wire is inappropriate for advancement to the desired position in a vessel. For example, the diameter of the guide wire may be too large for advancement past an extensive stenosis or occlusion in a vessel or for advancement in another relatively small vessel. The diameter of the guide wire may also be too small for effective advancement of the guide wire and catheter to the desired location in the vessel.

It may also be determined that the shape or construction of the guide wire is inappropriate for advancement of the guide wire to the desired position after the guide wire and catheter are in the vessel. For example, a distal portion of the guide wire is often bent a desired amount prior to insertion into the body of a patient to allow manipulation of the guide wire through various vessels. After the guide wire is in a vessel, it may be determined that a guide wire with a different "bend" is necessary to advance further to the desired position in the vessel or to advance into another vessel. The distal tip of the guide wire may also acquire an inappropriate bend during advancement of the guide wire in the vessel. For example, the distal tip of the guide wire may prolapse when movement of the tip is impeded and the guide wire is advanced further in the vessel.

When it is determined that the configuration of the guide wire is inappropriate for advancement in the vessel, the guide wire is typically exchanged for a guide wire having the desired configuration. With an over-the-wire type catheter, the guide wire can be withdrawn through the lumen of the catheter and a second guide wire can be installed while leaving the catheter in position. However, with a single-operator exchange type catheter, a guide wire exchange cannot readily be performed without withdrawing the catheter. Once the distal end of the first guide wire is withdrawn proximally from the proximal guide wire lumen opening of the catheter, a second guide wire cannot readily be positioned in the proximal guide wire lumen opening without also withdrawing the catheter so that the proximal guide wire lumen opening is outside the body of a patient.

To derive the benefits achieved from use of an over-the-wire catheter and a single operator exchange catheter, while overcoming the deficiencies of each, Scopton et al. disclose a convertible catheter assembly which includes both an over-the-wire capability and a single operator exchange capability. The Scopton et al. disclosure is made in PCT Application No. WO 92/17236, published on Oct. 15, 1992 and entitled "ADJUSTABLY STIFFENABLE CONVERTIBLE CATHETER ASSEMBLY". The disclosure of Scopton et al. is incorporated herein by reference. The Scopton et al. design includes three separate lumens in the proximal portion of the catheter shaft including an inflation lumen, a guide wire lumen and a stiffening mandrel lumen. A side hole is provided through the wall of the catheter shaft at a location close to a distal portion of the catheter. The side hole extends into the guide wire lumen, and has a valve-like cover flap. As is typical for most rapid-exchange type catheters, the column strength of the catheter shaft at the location of the side hole is significantly reduced. Thus, a problem with many rapid exchange type catheters is that the catheter may kink or otherwise fail at the location of the side hole.

When the system design is used in the over-the-wire configuration, a guide wire extends through the full length of the guide wire lumen as described above, and provides additional column support for the entire catheter shaft. A stiffening mandrel is also provided in the stiffening mandrel lumen to provide additional column support. The stiffening mandrel extends out of the proximal end of the catheter shaft, and can be selectively inserted or withdrawn within the stiffening mandrel lumen to control or vary the stiffness of the catheter shaft.

When the Scopton design is used in the rapid-exchange configuration, the guide wire occupies a position adjacent and exterior to the shaft along proximal and intermediate portions of the catheter, and enters a short guide wire lumen of the catheter via the side hole. Thus, in this configuration, the guide wire does not provide additional column support to a majority of the catheter shaft, including at and just proximal to the side hole. This is particularly problematic since the distal portion of the catheter is typically formed from a more flexible material than the proximal portion to facilitate the trackability of the catheter over the guide wire. To compensate for this, Scopton et al. suggest providing the distal most end of the stiffening mandrel distal of the location of the side hole. Thus, the stiffening mandrel may provide some support to the distal end of the catheter, and particular the portion adjacent the side hole. Scopton et al. also suggest that a second stiffening mandrel may be placed in the guide wire lumen proximal of the side hole, providing additional column support to the portion of the catheter shaft that is proximal of the side hole.

A limitation of the Scopton et al. design is that the force provided to the stiffening mandrel during navigation of the catheter through the vascular must be transmitted back to the proximal end of the catheter shaft, which may be a substantial distance. Further, the lumen that receives the stiffening mandrel has a diameter that allows the stiffening mandrel to laterally move therein. Under some circumstances, the stiffening mandrel may bend or otherwise become deformed within the lumen, thereby reducing the effectiveness of the force transmission provided thereby. Another limitation is that the stiffening mandrel does not directly support the weakest portion of the catheter shaft, namely, the portion adjacent the side port. The regions of the catheter that the stiffening mandrel engages during a particular procedure is arbitrary and unpredictable, and highly dependent on the shape of the tortuous path traversed by the catheter. There is therefore a need in the art for a catheter design that increases the force transmission from a stiffening mandrel or core wire to a stiffer more proximal portion of the catheter. There is also a need in the art for a catheter design that directly provides column support at or near the side port of a convertible or rapid exchange type of catheter.

SUMMARY OF THE INVENTION

Briefly stated, the present invention is directed to a method and apparatus for increasing the force transmission from a core wire to a more proximal portion of the catheter, and for directly providing column support at or near the side port of a convertible or rapid-exchange type of catheter. A core wire is typically attached to a proximal portion of a catheter, and extends distally therefrom through a lumen in the catheter. In accordance with the present invention, the core wire has a size and shape relative to the lumen of the catheter such that the lateral movement of the core wire is restricted in a restriction region. It has been found that by restricting lateral movement of the core wire at a distal location relative to the proximal catheter portion, the force transmission from the core wire to the proximal catheter portion can be increased. Further, in a rapid exchange or convertible type configuration, the restriction region may be placed; proximate the side hole. By restricting the movement of the core wire adjacent to the side hole, the core wire can provide direct column support thereto reducing the likelihood of kinking or the like at that location.

It is contemplated that the restriction region may extend the entire length of the core wire or any portion thereof. When the restriction region extends over the entire core wire, the core wire may provide additional column support to a substantial portion of the catheter shaft. Likewise, the force transmission from the distal end of the core wire to the proximal end would be substantially increased.

In one illustrative embodiment of the present invention, a shaft having a proximal portion and distal portion is provided. The distal portion is made flexible to increase the trackability of the catheter over the guide wire. The proximal portion of the shaft is made less flexible than the distal portion to increase the column strength, and thus the pushability of the catheter. A lumen extends longitudinally through the shaft of the catheter and has a restriction region distally of the proximal portion of the shaft. A core wire, operably attached to the proximal portion of the shaft, extends distally through the lumen and into the restriction region. The core wire has a size and shape relative to the restriction region of the lumen such that the lateral movement of the core wire is restricted more in the restriction region than outside of the restriction region.

To restrict the movement of the core wire in the restriction region, it is contemplated that the core wire may have an increased dimension in the restriction region, or the lumen of the shaft may have a reduced dimension, or a combination thereof. To decrease the dimension of the lumen of the shaft, an insert tube may be provided at a location that corresponds to the restriction region. To increase the dimension of the core wire, a restriction tube, bump or a bend may be provided at a location that corresponds to the restriction region. Likewise, the core wire may have a flattened portion, wherein the flattened portion has an increased outer dimension relative to a non-flattened portion. The flattened portion of the core wire may further be twisted, preferably between 90 and 360 degrees.

In another illustrative embodiment, a catheter is provided that has an outer tube, a distal inner tube and a proximal inner tube. The proximal inner tube is stiffer than the distal inner tube. The distal end of the proximal inner tube is attached to the proximal end of the distal inner tube, thereby forming an inner tube assembly. The inner tube assembly is disposed within the lumen of the outer tube, and has an outer surface that is spaced from at least a portion of the inner surface of the outer tube, defining a core wire receiving lumen therebetween. The core wire receiving lumen has a restriction region and a non-restriction region, as described above. The core wire is disposed in the core wire receiving lumen, and attached to the stiffer proximal inner tube. The core wire has a size and shape relative to the core wire receiving lumen such that lateral movement of the core wire is restricted more in the restriction region than in the non-restriction region The catheter may include a balloon secured proximate the distal end of the catheter. In this configuration, the core wire receiving lumen may also function as an inflation lumen. As indicated above, the tolerance between the core wire and the inner surface of the core wire receiving lumen is preferably greater in the non-restriction region than in the restriction region. Because the core wire receiving lumen may function as an inflation lumen, the core wire may have an outer surface that is shaped relative to the core wire receiving lumen such that lateral movement of the core wire is restricted more in the restriction region that in the non-restriction region, and also allows substantial fluid flow past the restriction region.

The inner tube assembly preferably has a guide wire lumen extending therethrough. In an over-the-wire configuration, the guide wire is provided through the guide wire lumen, and out the distal end thereof. To provide a rapid-exchange configuration, a side port is provided through the outer tube and inner tube assembly to provide access to the guide wire lumen. Preferably, the restriction region is proximate the side port so that the core wire can provide direct column support thereto.

In yet another illustrative embodiment, a catheter is provided that has an outer tube, a proximal inner tube and an inflation tube. The proximal inner tube is disposed within a proximal portion of the lumen of the outer tube. The inflation tube is also disposed in the lumen of the outer tube, adjacent the proximal inner tube, but extends nearly the full length of the outer tube. A guide wire lumen extends through the proximal inner tube and distally between the inner surface of the outer tube and the outer surface of the inflation tube. A core wire is preferably attached to the proximal inner tube extending distally in the guide wire lumen.

To provide a core wire restriction mechanism, a guide wire receiving tube may be provided in the guide wire lumen distal of the proximal inner tube. The guide wire receiving tube is preferably attached to the inner surface of the outer tube, and laterally spaced from at least a portion of the inflation tube. Thus, a restriction lumen is formed between the restriction tube and the inflation tube. A distal portion of the core wire extends through the restriction lumen. The core wire has a size and shape relative to the restriction lumen such that lateral movement of the core wire is restricted more in the restriction lumen than outside of the restriction lumen.

In an over-the-wire configuration, the guide wire may be provided through the guide wire lumen, through the guide wire receiving tube, and out the distal end of the catheter. In a rapid-exchange configuration, a side port is provided through the outer tube and the guide wire receiving tube to provide access to the guide wire lumen. The guide wire may then extend through the side port, into the guide wire receiving lumen, and out the distal end of the catheter. Preferably, the restriction region is proximate the side port so that the core wire can provide direct column support thereto.

The present invention, together with further objects and advantages, will be best understood by reference to the following detailed description taken in conjunction with the accompanying drawings.

BRIEF DESCRIPTION OF THE DRAWINGS

FIG. 1 is a side view, partially in section, of a first illustrative convertible balloon dilation catheter of the present invention;

FIG. 2 is a cross-sectional view of the catheter of FIG. 1, taken along the line 2—2;

FIG. 3 is a cross-sectional view of the catheter of FIG. 1, taken along the line 3—3;

FIG. 6 is a side view, partially in section, of a second illustrative convertible dilatation catheter of the present invention;

FIG. 7 is a cross-sectional view of the catheter of FIG. 6, taken along the line 7—7;

FIG. 8 is a perspective view of a flattened core wire in accordance with the present invention;

FIG. 9 is a perspective view of the flattened core wire of FIG. 8 after it is twisted;

FIG. 10 is a perspective view of an "X" shaped core wire in accordance with the present invention;

FIG. 11 is a perspective view of a core wire having a restriction tube placed therearound;

FIG. 12 is a perspective view of a core wire having a bump or bend therein;

FIG. 13 is an expanded side view, partially in section, of the convertible catheter of FIG. 6, detailing a flexible valve;

FIG. 14 is a perspective view, partially in section, of the side hole and preferred valve mechanism of FIG. 13;

FIG. 15 is a perspective view of the preferred valve mechanism of FIG. 14; and

FIG. 16 is a side view, partially in section, of another illustrative convertible balloon dilation catheter of the present invention including a movable sleeve for selectively covering the side opening.

DETAILED DESCRIPTION OF THE PREFERRED EMBODIMENT

Figure 4:
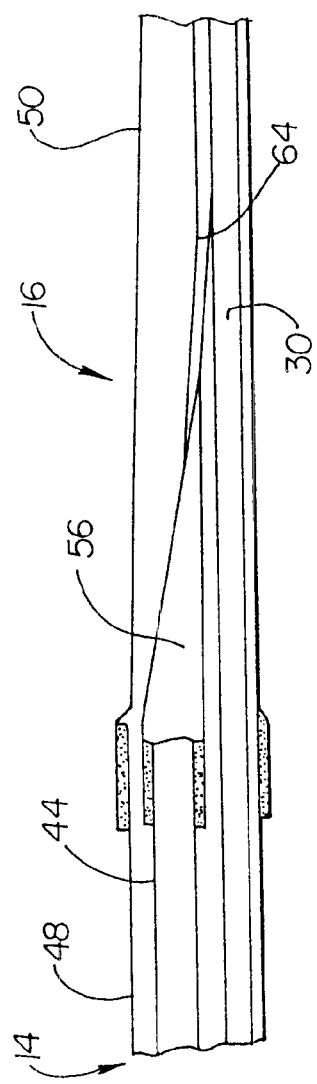
FIG. 4 is an expanded partial cross-sectional side view of the intersection of the proximal and distal portions of the catheter of FIG. 1.

The presently preferred embodiments and methodology described herein are applicable to coronary angioplasty procedures and are specifically described in the context of convertible dilation balloon catheters. It should be understood, however, that the embodiments and methodology of the present invention may be adapted for use with other types of catheters.

Referring to FIG. 1, a first embodiment of a convertible balloon dilatation catheter is generally shown at 10. The catheter 10 includes a shaft 12 having a proximal portion 14 and a distal portion 16. A dilatation balloon 18 is located at and connected to the distal portion 16 of the catheter shaft 12. The distal portion 16 of the shaft 12 extends into the proximal opening 20 in the balloon 18 and is preferably connected to the proximal neck portion 22. The distal portion 16 of the shaft 12 has a reduced diameter portion 24 that extends through the distal opening 26 in the balloon. 18 and is preferably connected to the distal neck portion 28.

The shaft 12 includes an inflation lumen 30 extending therethrough that has a proximal opening and a distal opening 34. A distal portion of the inflation lumen extends through the distal portion 16 of the shaft 12, as generally shown at 40. A manifold 36 is connected to the proximal portion 14 of the shaft 12, and is in fluid communication with the interior 38 of the dilation balloon 18 via the inflation lumen 30. Inflation fluid is conveyed via inflation lumen 30 from the manifold 36 to inflate the balloon 18 and therefore dilate a vessel in a conventional manner known in the art.

In the illustrative embodiment, the proximal portion 14 of the shaft 12 includes a proximal inner tube 44 and the proximal portion of inflation tube 30. The proximal inner tube 44 preferably only extends to an intermediate portion of the catheter, as shown. The proximal inner tube 44 is disposed adjacent to the inflation tube 30, and the combination is wrapped with an outer sleeve 48, as best seen in FIG. 2, The outer sleeve 48 is preferably made from a heat shrink material.

The distal portion 16 of the shaft 12 includes a distal outer tube 50 and the distal portion of the inflation tube 30 extending therein. The distal outer tube 50 is preferably more flexible than the proximal inner tube 44. By making the distal outer tube 50 of the catheter more flexible, the catheter may more readily track a guide wire through a tortuous path. By making the proximal inner tube 44 less flexible, the column strength and pushability of the catheter shaft may be increased. In a preferred embodiment, the proximal inner tube 44 is a metallic hypotube formed from stainless steel, Nitinol or the like, and the distal outer tube 50 is formed from HDPE, Marlex™, Vestamide™, or a blend of these or other polymeric materials. The distal outer tube is secured around the distal end of the proximal portion 14 of the catheter shaft 12.

To provide a transition in flexibility from the proximal portion 14 to the distal portion 16 of the shaft 12, a strain relief member 56 may be provided. The strain relief member 56 preferably is formed by cutting off the distal end of the proximal inner tube 44 at an angle. Alternatively, the strain relieve member 56 may be a separate element that provides the desired transition in flexibility.

A core wire 64 is preferably attached to the proximal inner tube 44. The core wire 64 extends distally from the proximal inner tube 44 and into the guide wire lumen 52. The core wire 64 transfers force from the distal portion 16 of the catheter to the stiffer proximal inner tube 44, particularly when the catheter is being pushed through a tight stenosis. The core wire 64 also provides some degree of column support to the distal portion 16 of the catheter shaft.

In the illustrative embodiment, a guide wire receiving tube 62 having a guide wire receiving lumen 63 may be provided in the guide wire lumen 52 distal of the proximal inner tube 44, as shown. The guide wire receiving tube 62 is preferably attached to the upper side wall of the distal outer tube 50 by a suitable adhesive 70, and is laterally spaced from at least a portion of the inflation tube 30. A restriction lumen is thus formed between the guide wire receiving tube and an outer surface of the inflation tube 30. A distal portion of the core wire 64 extends through the restriction lumen, as can best be seen in FIG. 3. The core wire 64 has a size and shape relative to the restriction lumen such that lateral movement of the core wire 64 is restricted more in the restriction lumen than outside of the restriction lumen. In the embodiment shown, the core wire 64 is preferably friction fit in the restriction lumen so that longitudinal movement is also restricted to a degree.

A guide wire lumen 52 extends from the manifold 36, through the proximal inner tube 44, through the guide wire receiving tube, through the reduced diameter portion 24 and out the distal end of the catheter. A guide wire may be provided through the full length of the guide wire lumen 52 to operate in an over-the-wire configuration. In a rapid-exchange configuration, a side hole or port 60 may be provided through the distal outer tube 50 and the guide wire receiving tube 62 to provide access to the guide wire lumen 52. A guide wire may then extend through the side port 60, into the guide wire receiving lumen 63 of the guide wire receiving tube 62, and out of the distal end of the catheter. Preferably, the guide wire receiving tube 62 is proximate the side port 60. In addition, a stylet or the like may be provided in the guide wire lumen 52 proximal of the side hole 60 to provide additional column support to the proximal portion of the catheter.

In accordance with the present invention, it has been found that by restricting the core wire 64 at a distal location relative to the proximal inner tube 44, the force transmission from the core wire 64 to the proximal inner tube 44 can be increased. Further, in a rapid exchange or convertible type configuration, by placing the restriction region proximate the side port 60, the core wire 64 can provide direct column support thereto, reducing the likelihood of kinking or the like at that location.

FIG. 4 is an expanded side view of the intersection of the proximal portion 14 and distal portion 16 of the catheter 10 of FIG. 1. As indicated above, the proximal portion 14 of the shaft 12 includes a proximal inner tube 44 and the proximal portion of the inflation tube 30. The inflation tube 30 preferably extends from the manifold 36 to the interior 38 of the balloon 18, while the proximal inner tube 44 preferably only extends to an intermediate portion of the catheter, as shown. The proximal inner tube 44 is disposed adjacent to the inflation tube 30, and the combination is wrapped with an outer sleeve 48, as best seen in FIG. 2, The outer sleeve 48 is preferably made from a heat shrink material.

The distal portion 16 of the shaft 12 includes a distal outer tube 50, with the distal portion of the inflation tube 30 extending therein. The distal outer tube 50 is preferably more flexible than the proximal inner tube 44. By making the distal outer tube 50 of the catheter more flexible, the catheter may more readily track a guide wire through a tortuous path. By making the proximal inner tube 44 less flexible, the column strength and pushability of the catheter shaft may be increased.

To provide a transition in flexibility from the proximal portion 14 to the distal portion 16 of the shaft 12, a strain relief member 56 may be provided. The strain relief member 56 preferably is formed by cutting off the distal end of the proximal inner tube 44 at an angle. Alternatively, the strain relieve member 56 may be a separate element that is attached to the distal end of the proximal inner tube 44, and provides the desired transition in flexibility.

A core wire 64 is attached to the proximal inner tube 44. The core wire 64 extends distally from the proximal inner tube 44 and into the guide wire lumen 52. The core wire 64 transfers force from the distal portion 16 of the catheter to the stiffer proximal inner tube 44, particularly when the catheter is being pushed through a tight stenosis.

Figure 5:
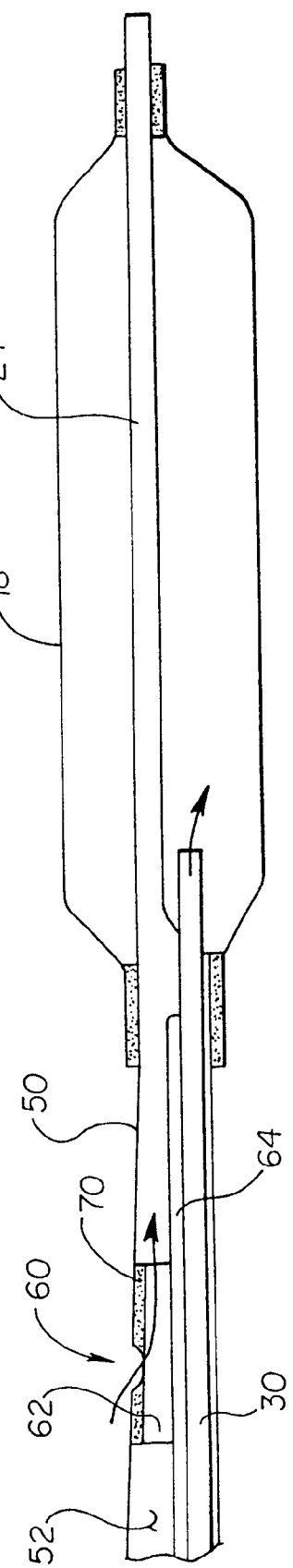
FIG. 5 is an expanded partial cross-sectional side view of the distal portion of the catheter of FIG. 1 including the guide wire receiving tube.

FIG. 5 is an expanded side view, partially in section, of the distal portion of the catheter of FIG. 1 including the guide wire receiving tube 62. As indicated above, the guide wire receiving tube 62 may be provided in the guide wire lumen 52 distal of the proximal inner tube 44, as shown. The guide wire receiving tube 62 is preferably attached to the upper side wall of the distal outer tube 50 by a suitable adhesive 70 or heat bond, and is laterally spaced from at least a portion of the inflation tube 30, thereby forming a restriction lumen therebetween. A distal portion of the core wire 64 extends through the restriction lumen, as shown. The core wire.64 has a size and shape relative to the restriction lumen such that lateral movement of the core wire 64 is restricted more in the restriction lumen than outside of the restriction lumen. In the embodiment shown, the core wire 64 is preferably friction fit in the restriction lumen so that longitudinal movement is also restricted to a degree.

A guide wire lumen 52 extends from the manifold 36, through the proximal inner tube 44, through the guide wire receiving tube 62, through the reduced diameter portion 24 of the distal outer 50, and out the distal end of the catheter. In an over-the-wire configuration, a guide wire may be provided through the full length of the guide wire lumen 52, including through the guide wire receiving tube 62. In a rapid-exchange configuration, a side hole or port 60 may be provided through the distal outer tube 50 and the guide wire receiving tube 62 to access the guide wire lumen 52. A guide wire may then extend through the side port 60, into the guide wire receiving lumen 63 (see FIG. 3) of the guide wire receiving tube 62, and out of the distal end of the catheter. Preferably, the guide wire receiving tube 62 is proximate the side port 60 so that the core wire 64 can provide direct column support thereto.

Referring now to FIG. 6, a second illustrative convertible dilatation catheter of the present invention is generally shown at 100. The catheter has an outer tube 102, a distal inner tube 104 and a proximal inner tube (not shown). Like the embodiment shown in FIG. 1, the proximal inner tube is preferably stiffer than the distal inner tube 104. The distal end of the proximal inner tube is attached to the proximal end of the distal inner tube, thereby forming an inner tube assembly 106.

The inner tube assembly 106 is disposed within the lumen 107 of the outer tube 102 in a coaxial arrangement, and has an outer surface 108 that is spaced from at least a portion of the inner surface 110 of the outer tube 102, defining a core wire receiving lumen 112 therebetween. The core wire receiving lumen 112 has a restriction region 114 and a non-restriction region 116, as described above. A core wire 120 is disposed in the core wire receiving lumen 112, and is attached to the stiffer proximal inner tube. The core wire 120 has a size and shape relative to the core wire receiving lumen 112 such that lateral movement of the core wire is restricted more in the restriction region 114 than in the non-restriction region 116.

A dilatation balloon 118 is located at and connected to the distal portion of the catheter shaft. The distal end of the outer tube 102 is connected to the proximal neck portion 122 of the balloon 118. The distal inner tube extends through the balloon, and is connected to the distal neck portion of the balloon 118.

The core wire receiving lumen 112 also functions as an inflation lumen in this embodiment. Thus the core wire receiving lumen 112 extends from the proximal end of the catheter and is in fluid communication with the balloon 118. The inner tube assembly 106 includes a guide wire lumen 115 extending therethrough for receiving a guide wire. The guide wire lumen 115 extends from the proximal end of the catheter to the distal end of the catheter.

A side port 124 is preferably provided through the side of the outer tube 102 and through the side of the distal inner tube 104, and into the guide wire lumen 115. The side port 124 is preferably located within 7 cm of the distal end of the catheter. In a preferred embodiment, the distal inner tube 104 is secured to the inner surface of the outer tube 102 at the location of the side port 124. This allows the side port 124 to more directly access the guide wire lumen 115 of the distal inner tube 104. A flexible flap or valve 125 is preferably placed over the side port 124.

In an over-the-wire configuration, a guide wire (not shown) is provided through the entire length of the guide wire lumen 115, and out the distal end of the catheter. In this configuration, the flexible flap 125 is in a closed position, covering the side port 124. In a rapid exchange configuration, the guide wire extends through the side port 124, into the guide wire lumen 115, and out the distal end of the catheter. In this configuration, the flexible flap 125 is in an open or deflected position, allowing the guide wire to access the guide wire lumen 115.

Preferably, the distal inner tube 104 is offset from the central longitudinal axis of the outer tube 102 near the side port 124 and heat bonded thereto. This is preferably accomplished by inserting a mandrel between the distal inner tube 104 and the inner wall of the outer tube 102, and then applying heat and an inward pressure around the outer tube, and in particular, in the region near the side port 124. The inward pressure presses the distal inner tube against the inner surface of the outer tube 102. The heat softens the plastic material of the distal inner tube 104 and the outer tube 102 forming a heat bond therebetween, as more clearly shown in FIG. 7.

The mandrel preferably has a shape that corresponds to the desired shape of the core wire receiving lumen 112 (inflation lumen) in the restriction region. The applied heat and inward pressure cause the plastic material of the distal inner tube 104 and the outer tube 104 to flow around the mandrel and provide a core wire receiving lumen having the desired shape. A mandrel may also be provided in the guide wire lumen to maintain the size and shape thereof during the heating process.

FIG. 7 shows a cross-sectional view of the catheter of FIG. 6, taken along the line 7—7. As indicated above, the tolerance between the core wire 120 and the inner surface of the core wire receiving lumen 112 is preferably greater in the non-restriction region 116 than in the restriction region 114. Because the core wire receiving lumen 112 may also function as an inflation lumen, the core wire 120 may have an outer surface that is shaped relative to the core wire receiving lumen 112 such that lateral movement of the core wire is restricted more in the restriction region 114 that in the non-restriction region 116, but also allows substantial fluid flow past the restriction region. This may be particularly helpful when the core wire receiving lumen is substantially round in the restriction region.

FIG. 8 shows a core wire 140 having a flattened portion 142, wherein the flattened portion has an increased outer dimension relative to the non-flattened portion. This may allow the movement of the core wire to be more restricted in the restriction region 114. The flattened portion 142 of the core wire 140 may be twisted, preferably between 90 and 360 degrees, as shown in FIG. 9. Twisting the flattened portion 142 may help the flexibility of the core wire 140 to be about equally in all directions. The flattened portion, whether twisted or not, provides a path through which inflation fluid can pass through the restriction region.

It is contemplated that the restriction region may extend over the entire core wire or any portion thereof. When the restriction region extends over the entire core wire, the core wire may provide additional column support to the entire corresponding catheter shaft. Likewise, the force transmission from the distal end of the core wire to the proximal end is increased. Accordingly, the core wire may have a close tolerance or be friction fit in the core wire receiving lumen along the entire length of the core wire.

FIG. 10 shows an "X" shaped core wire 150. The "X" shaped core wire 150 may be particularly suitable when the restriction region extends over a substantial length of the core wire, and also functions as an inflation lumen. The "X" shaped core wire may have a close tolerance (or be friction fit) to the core wire receiving lumen, while still providing a path for the inflation fluid to pass through the restriction region.

FIG. 11 shows a core wire 156 having a restriction tube 158 placed therearound. The restriction tube 158 is preferably placed at a location on the core wire 156 that corresponds to the restriction region in the core wire receiving lumen. The restriction tube 158 increases the outer dimension of the core wire 156 so that lateral movement of the core wire is restricted more in the restriction region that in the non-restriction region.

FIG. 12 shows yet another core wire 160. Core wire 160 includes a bend or bump therein that is preferably placed at a location that corresponds to the restriction region in the core wire receiving lumen. The bend or bump 162 increases the outer dimension of the core wire 160 so that lateral movement of the core wire 160 is restricted more in the restriction region that in the non-restriction region.

FIG. 13 shows an expanded view of the convertible catheter of FIG. 6, detailing the flexible valve or gate 125. The flexible valve or gate 125 can be positioned in a closed position or an open position. In the closed position, the flexible valve covers the side port 124, as shown at 180. In the open position, the flexible valve 125 opens the side port 124 to the guide wire lumen 115, as shown at 182. In an over-the-wire configuration, the flexible valve 125 is placed in the closed position. This may prevent the distal end of the guide wire from inadvertently exiting the guide wire lumen through the side port 124 when the catheter is threaded over the guide wire, and may further prevent blood or the like from entering the guide wire lumen 115 during a procedure. In a rapid exchange configuration, the flexible valve 125 is placed in the open position, thereby allowing a guide wire to gain access to the guide wire lumen 115 via the side port 124.

The flexible value 125 is preferably made from a flexible material that can be easily manipulated into a closed and open position. This can include polymeric materials or metals such as Nitinol. FIGS. 14–15 show a preferred valve 200. Valve 200 has an attachment region 202 and a flap 204. The attachment region preferably includes a receiving portion 205 for receiving the distal inner tube 104. The flap 204 extends along the outer surface of the distal inner tube 104, and over the side hole 208 provided therein.

In this embodiment, the side hole 208 in the distal inner tube 104 is larger than the side hole 124 provided in the outer tube 102. This allows the flap 204 to completely cover and overlap the side hole 124 in the outer tube 102 in the closed position, while still allow the flap 204 to be pushed into the guide wire lumen of the distal inner tube 104 in the open position.

As can be seen, the flap 204 is normally in the closed position covering the side hole 124. By applying inward pressure, however, the flap 204 can be flexed or bent inwardly as shown, allowing access to the guide wire lumen 115. The flap 204 may be made from any suitable flexible plastic or metallic material.

FIG. 16 shows an illustrative convertible balloon dilation catheter similar to that of FIG. 13, but further includes a movable sleeve for selectively covering the side opening. In this embodiment, a sleeve 250 is provided over the outside surface of the catheter shaft. The sleeve 250 can be moved longitudinally along the catheter shaft, as indicated by arrows 254. The sleeve 250 is preferably controlled by a shaft 252, which extends from the sleeve 250 to the proximal end of the catheter. By manipulating the shaft 252, the sleeve may be moved, for example, from an open position 260 which does not cover side opening 124, to a closed position 262 which covers side opening 124.

In an over-the-wire configuration, the sleeve 250 is positioned in the closed position 260 by moving the proximal end of the shaft 252 distally until the sleeve covers the side port 124. By covering the side port 124, the distal end of the guide wire may be prevented from inadvertently exiting the guide wire lumen through the side port 124 when the catheter is threaded over the guide wire, and may further prevent blood or the like from entering the guide wire lumen 115 via the side port 124 during a procedure. In a rapid exchange configuration, the sleeve 250 is positioned in the open position 262 by moving the proximal end of the shaft 252 proximally until the sleeve is proximal of the side port 124. This provides a guide wire access to the guide wire lumen 115 via the side port 124.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the following claims, including all equivalents thereof, which are intended to define the scope of the invention.

What is claimed is:

1. A catheter comprising:
    an outer tube having an inner surface that defines a lumen therein;
    an inner tube disposed within the lumen of the outer tube, the inner tube having an outer surface that is spaced from at least a portion of the inner surface of the outer tube defining a core wire receiving lumen therebetween;
    the core wire receiving lumen having a restriction region and a non-restriction region;
    the outer tube having an access port therethrough into the core wire receiving lumen proximate the restriction region; and
    a core wire disposed within the core wire receiving lumen and extending distally of the access port, the core wire having a size and shape relative to the restriction region such that lateral movement of the core wire is restricted more in the restriction region that in the non-restriction region.

2. A catheter according to claim 1 wherein the core wire receiving lumen has substantially the same dimensions in the restriction region and the non-restriction region, and the core wire has selected increased outer dimensions at a location that corresponds to the restriction region.

3. A catheter according to claim 2 wherein the core wire includes an outwardly extending bump at a location that corresponds to the restriction region.

4. A catheter according to claim 1 wherein the core wire has substantially the same outer dimensions in the restriction region and the non-restriction region, and the core wire receiving lumen has a reduced dimension of the core wire receiving lumen in the restriction region.

5. A catheter according to claim 4 wherein the core wire receiving lumen includes an insert tube for reduced dimension of the core wire receiving lumen in the restriction region.

6. A catheter according to claim 1 wherein the core wire receiving lumen has a tighter tolerance to the core wire in the restriction region than in the non-restriction region.

7. A catheter according to claim 1 wherein the core wire has a flattened portion at a location that corresponds to the restriction region, the flattened portion having an increased outer dimension relative to a non-flattened portion of the core wire.

8. A catheter comprising:
    an outer tube having an inner surface that defines a lumen therein;
    a distal inner tube having a proximal end and a distal end;
    a proximal inner tube having a proximal end and a distal end, the distal end of the proximal tube operably attached to the proximal end of the distal inner tube, thereby forming an inner tube assembly;
    the inner tube assembly disposed within the lumen of the outer tube, the inner tube assembly having an outer surface that is spaced from at least a portion of the inner surface of the outer tube, defining a core wire receiving lumen therebetween;
    the core wire receiving lumen having a restriction region and a non-restriction region; and
    a core wire disposed in the core wire receiving lumen, and operably attached to the proximal inner tube and extending distally therefrom, the core wire having a size and shape relative to the core wire receiving lumen such that lateral movement of the core wire is restricted more in the restriction region that in the non-restriction region.

9. A catheter according to claim 8 further comprising a balloon with a balloon interior operably attached to a distal end of the catheter.

10. A catheter according to claim 9 wherein the core wire receiving lumen is also an inflation lumen, and is in fluid communication with the balloon interior.

11. A catheter according to claim 10 wherein the tolerance between the core wire and the inner surface of the core wire receiving lumen is greater in the nonrestriction region than in the restriction region.

12. A catheter according to claim 11 wherein the core wire has an outer surface that is shaped relative to the core wire receiving lumen such that lateral movement of the core wire is restricted more in the restriction region than in the non-restriction region, but allows substantial fluid flow past the restriction region.

13. A catheter according to claim 8 wherein the inner tube assembly has a guide wire lumen therein.

14. A catheter according to claim 13 wherein the outer tube and the inner tube assembly have a side port extending laterally therethrough and into the guide wire lumen.

15. A catheter according to claim 14 wherein the restriction region of the core wire receiving lumen is proximate the side port.

16. A catheter according to claim 15 wherein the restriction region of the core wire receiving lumen is proximal of the side port.

17. A catheter according to claim 8 wherein the distal inner tube is more flexible than the proximal inner tube.

18. A catheter according to claim 8 wherein the distal inner tube is a plastic, and the proximal inner tube is a metallic hypotube.

19. A catheter comprising:
an outer tube having an inner surface that defines a lumen therein, the outer tube having a proximal end and a distal end;
a proximal inner tube having a proximal end and a distal end disposed within the lumen of the outer tube, the distal end of the outer tube extending distally of the distal end of the proximal inner tube;
a guide wire receiving tube having a guide wire receiving lumen therein disposed in the lumen of the outer tube distally of the distal end of the proximal inner tube, said guide wire receiving tube spaced from at least a portion of the inner surface of the outer tube thereby forming a restriction lumen therebetween;
a core wire operable attached to the proximal inner tube and extending distally therefrom, the core wire extending through the restriction lumen; and
the core wire having a size and shape relative to the restriction lumen such that lateral movement of the core wire is restricted more in the restriction lumen than outside of the restriction lumen.

20. A catheter according to claim 19 wherein the proximal inner tube has a lumen extending therethrough.

21. A catheter according to claim 20 further comprising a guide wire extending through the lumen of the proximal inner tube and the guide wire receiving lumen.

22. A catheter according to claim 19 wherein an opening is provided through the outer tube and the guide wire receiving tube to expose the guide wire receiving lumen to the exterior of the outer tube.

23. A catheter comprising:
an outer tube having an inner surface that defines a lumen therein, the outer tube having a proximal end and a distal end;
a proximal inner tube having a proximal end and a distal end disposed within the lumen of the outer tube, the distal end of the outer tube extending distally of the distal end of the proximal inner tube;
an inflation tube having a proximal end and a distal end and an inflation lumen extending therethrough, the inflation tube being disposed within the lumen of the outer tube, the proximal end of the inflation tube being proximal of the distal end of the proximal inner tube and the distal end of the inflation tube extending distally of the distal end of the proximal inner tube
a guide wire receiving tube having a guide wire receiving lumen therein disposed in the lumen of the outer tube distally of the distal end of the proximal inner tube and proximal of the distal end of the inflation tube, said guide wire receiving tube spaced from at least a portion of the inflation tube, thereby forming a restriction lumen therebetween;
a core wire operable attached to the proximal inner tube and extending distally therefrom, the core wire extending through the restriction lumen; and
the core wire having a size and shape relative to the restriction lumen such that lateral movement of the core wire is restricted more in the restriction lumen than outside of the restriction lumen.

24. A catheter according to claim 23 wherein the proximal inner tube has a lumen extending therethrough.

25. A catheter according to claim 24 further comprising a guide wire extending through the lumen of the proximal inner tube and the guide wire receiving lumen.

26. A catheter according to claim 23 wherein an opening is provided through the outer tube and the guide wire receiving tube to expose the guide wire receiving lumen to the exterior of the outer tube.

27. A catheter comprising:
an outer tube having an inner surface that defines a lumen therein;
an inner tube disposed within the lumen of the outer tube, the inner tube having an outer surface that is spaced from at least a portion of the inner surface of the outer tube defining a core wire receiving lumen therebetween; and
a core wire disposed within the core wire receiving lumen, the core wire having a size and shape relative to the core wire receiving lumen to substantially prevent lateral movement of the core wire therein, the core wire having an outer boundary defined by the edges of a lateral cross-section of the core wire, said outer boundary engaging both the inner surface of the outer tube and the outer surface of the inner tube.

28. A catheter comprising:
an outer tube having an inner surface that defines a lumen therein;
an inner tube disposed within the lumen of the outer tube, the inner tube having an outer surface that is spaced from at least a portion of the inner surface of the outer tube defining a core wire receiving lumen therebetween;
the core wire receiving lumen having a restriction region and a non-restriction region;
a core wire disposed within the core wire receiving lumen, the core wire having a size and shape relative to the core wire receiving lumen such that lateral movement of the core wire is restricted more in the restriction region that in the non-restriction region; and
the core wire having a flattened portion at a location that corresponds to the restriction region, the flattened portion having an increased outer dimension relative to a non-flattened portion of the core wire, the flattened portion of the core wire is twisted to provide a twisted flattened portion.

29. A catheter according to claim 28 wherein the twisted flattened portion of the core wire is twisted between 90 and 360 degrees.

30. A catheter comprising:
an outer tube having an inner surface that defines a lumen therein;
a distal inner tube having a proximal end and a distal end;
a proximal inner tube having a proximal end and a distal end, the distal end of the proximal tube operably attached to the proximal end of the distal inner tube, thereby forming an inner tube assembly;

the inner tube assembly disposed within the lumen of the outer tube, the inner tube assembly having an outer surface that is spaced from at least a portion of the inner surface of the outer tube, defining a core wire receiving lumen therebetween;

the core wire receiving lumen having a restriction region and a non-restriction region; and a core wire disposed in the core wire receiving lumen, and operably attached to the proximal inner tube and extending distally therefrom, the core wire having a size and shape relative to the inner surface of the core wire receiving lumen to provide a frictional fit therebetween.

31. A catheter comprising:

an outer tube having an inner surface that defines a lumen therein, the outer tube having a proximal end and a distal end;

a proximal inner tube having a proximal end and a distal end disposed within the lumen of the outer tube, the distal end of the outer tube extending distally of the distal end of the proximal inner tube;

a guide wire receiving tube having a guide wire receiving lumen therein disposed in the lumen of the outer tube distally of the distal end of the proximal inner tube, said guide wire receiving tube spaced from at least a portion of the inner surface of the outer tube thereby forming a restriction lumen therebetween;

a core wire operable attached to the proximal inner tube and extending distally therefrom, the core wire extending through the restriction lumen; and the core wire having a size and shape relative to the restriction lumen such that the core wire is friction fit in the restriction lumen.

32. A catheter comprising:

an outer tube having an inner surface that defines a lumen therein, the outer tube having a proximal end and a distal end;

a proximal inner tube having a proximal end and a distal end disposed within the lumen of the outer tube, the distal end of the outer tube extending distally of the distal end of the proximal inner tube;

an inflation tube having a proximal end and a distal end and an inflation lumen extending therethrough, the inflation tube being disposed within the lumen of the outer tube, the proximal end of the inflation tube being proximal of the distal end of the proximal inner tube and the distal end of the inflation tube extending distally of the distal end of the proximal inner tube a guide wire receiving tube having a guide wire receiving lumen therein disposed in the lumen of the outer tube distally of the distal end of the proximal inner tube and proximal of the distal end of the inflation tube, said guide wire receiving tube spaced from at least a portion of the inflation tube, thereby forming a restriction lumen therebetween;

a core wire operable attached to the proximal inner tube and extending distally therefrom, the core wire extending through the restriction lumen; and the core wire having a size and shape relative to the restriction lumen such that the core wire is friction fit in the restriction lumen.

* * * * *